(12) United States Patent
Pérez Millán et al.

(10) Patent No.: US 11,851,795 B2
(45) Date of Patent: Dec. 26, 2023

(54) SYSTEM AND METHOD FOR CHARACTERIZATION OF PATTERNS MARKED ON A FABRIC

(71) Applicants: JEANOLOGIA, S. L., Paterna Valencia (ES); FYLA LASER, S. L., Paterna Valencia (ES)

(72) Inventors: Pere Pérez Millán, Paterna Valencia (ES); Salvador Torres Peiró, Paterna Valencia (ES); Jorge Pérez Vizcaíno, Paterna Valencia (ES); Ricardo Mira Paya, Paterna Valencia (ES)

(73) Assignees: JEANOLOGIA, S. L., Paterna Valencia (ES); FYLA LASER, S. L., Paterna Valencia (ES)

( * ) Notice: Subject to any disclaimer, the term of this patent is extended or adjusted under 35 U.S.C. 154(b) by 708 days.

(21) Appl. No.: 17/050,540

(22) PCT Filed: Apr. 24, 2019

(86) PCT No.: PCT/IB2019/053371
§ 371 (c)(1),
(2) Date: Oct. 26, 2020

(87) PCT Pub. No.: WO2019/207496
PCT Pub. Date: Oct. 31, 2019

(65) Prior Publication Data
US 2021/0238786 A1    Aug. 5, 2021

(30) Foreign Application Priority Data

Apr. 27, 2018 (EP) .................................. 18382293

(51) Int. Cl.
*G01J 3/10* (2006.01)
*D06B 11/00* (2006.01)
(Continued)

(52) U.S. Cl.
CPC ....... *D06B 11/0096* (2013.01); *G01N 21/255* (2013.01); *G01N 21/474* (2013.01);
(Continued)

(58) Field of Classification Search
CPC ......... G01N 21/956; G01N 2021/4764; G01N 2201/1042; G01J 3/10; G01J 3/46; G01J 3/502; G01J 3/4535
See application file for complete search history.

(56) References Cited

U.S. PATENT DOCUMENTS

| 3,986,778 A | 10/1976 | Mathisen et al. |
| 2010/0290032 A1 | 11/2010 | Bugge |
| 2015/0124336 A1* | 5/2015 | Kaufman ................. G01J 3/36 359/728 |

FOREIGN PATENT DOCUMENTS

| EP | 0 649 170 A2 | 4/1995 | |
| EP | 1090321 A1 * | 4/2001 | ............ B23K 26/02 |
| WO | 2018035538 A1 | 2/2018 | |

OTHER PUBLICATIONS

International Search Report and Written Opinion of the International Searching Authority dated Sep. 5, 2019 in corresponding International application No. PCT/IB2019/053371; 10 pages.
(Continued)

*Primary Examiner* — Rebecca C Bryant
(74) *Attorney, Agent, or Firm* — Maier & Maier, PLLC (57) ABSTRACT

A system and method for characterization of patterns marked on a fabric. The system includes a light source generating a light beam to impinge on a fabric; an optical arrangement including a parabolic mirror with a hole and an optical device, directing said light beam towards the fabric; a wavelength division unit; a light detection unit; and a computing device. The optical device changes and orients the direction of the light beam towards the fabric providing a scan of an area of the fabric, line-by-line, and redirects
(Continued)

scattered light towards the light detection unit. The wavelength division unit separates the scattered light into spectral bands or colors and the computing device characterizes a pattern marked on the fabric by executing an algorithm that analyzes electrical voltage signals and that computes a quality measure of said marked pattern.

15 Claims, 7 Drawing Sheets

(51) Int. Cl.
    *G01N 21/25*     (2006.01)
    *G01N 21/47*     (2006.01)
    *G01N 21/956*     (2006.01)

(52) U.S. Cl.
    CPC ... *G01N 21/956* (2013.01); *G01N 2021/4764* (2013.01); *G01N 2201/1042* (2013.01)

(56) References Cited

OTHER PUBLICATIONS

Tobin, et al., "Accommodating Multiple Illumination Sources in an Imaging Colorimetry Environment", Visual and communications and image processing, 2000, pp. 194-205; 12 p.

* cited by examiner

SYSTEM AND METHOD FOR CHARACTERIZATION OF PATTERNS MARKED ON A FABRIC

FIELD

The present invention is directed, in general, to the fields of optical characterization of materials and of laser techniques. In particular, the invention relates to a system and to a method for characterization of patterns marked on a fabric such as denim, among other types of fabrics.

BACKGROUND

US-A1-2010290032 provides a method and a system for measuring/depicting and determining/identifying one or more objects of different types of plastics, different types of fabrics or clothing, different types of glass, different types of food/groceries, different types of cardboard/paper/wooden products and/or different types of metals or similar materials. The method includes considering the reflected, scattered and/or transmitted light from the laser through the material, and determining the type of material from this.

WO-A1-2018035538 provides software and lasers which are used in finishing apparel to produce a desired wear pattern or other design. A technique includes determining a fabric's response to a laser, capturing an initial image of a wear pattern on a garment, and processing the initial image to obtain a working image in grayscale. The working image is further processed to obtain a difference image by comparing each pixel relative to a dark reference. The difference image is converted to a laser values image by using the previously determined fabric response to the laser.

The above patents are prior art regarding the characterization of materials (fabrics among them) by optical means. US-A1-2010290032 is limited by the use of monochromatic sources that have to be tuned or changed to illuminate at different wavelengths. WO-A1-2018035538 is limited by the lack of an objective measuring system and by the lack of a systematic numerical method for quantitative characterization.

Apart from that, U.S. Pat. No. 3,986,778 provides a spectrophotometer system especially adapted for analyzing the colors of textiles. A sample holder includes a base that clamps a textile sample on a supporting surface. Slidably mounted on the base is a slider that is movable between two positions. In one position, an opening exposes the area to be analyzed. In the other position, a fiber optic head assembly overlies the area to be analyzed, the assembly including at least one fiber optic bundle for projecting light onto the sample and at least one other fiber optic bundle for receiving light reflected from the sample. A switch is mounted at one end of the base and is actuated when the slider is in the other position so as to provide an electrical signal indicating that a reading may be taken or analyzed by the spectrophotometer.

Likewise, document Tobin K W et al. "Accommodating multiple illumination sources in an imaging colorimetry environment", Visual and communications and image processing; vol. 3966, 26 Jan. 2000, pages 194-205, discloses a method for measuring color quality in textile products using a tri-stimulus color camera system. The results of this method showed that the projection onto convex sets (POCS) approach to color estimation could be applied to complex printed patterns on textile products with high accuracy and repeatability. Image-based color sensors used for on-line measurement are not colorimetric by nature and require a non-linear transformation of the component colors based on the spectral properties of the incident illumination, imaging sensor, and the actual textile color.

Therefore, there is a need for an improved system and method for characterization of patterns marked on a fabric based on illumination of broadband spectrum in order to allow taking quantitative quality measurements of the marked pattern, for example the brightness contrast between parts of the pattern, the number of observable stripes of a striped pattern, the visibility curve of a striped pattern, a comparison with a pure white, etc.

SUMMARY

To that end, present invention provides according to a first aspect a system for characterization of patterns marked (or generated) on a fabric. The system as known in the field comprises a light source configured to generate a light beam, having a broadband spectrum (i.e. the light beam is composed by a large number of radiation components of different wavelengths that are emitted simultaneously by the light source), to impinge on a fabric located at a given distance and an optical arrangement configured to direct said light beam towards the fabric and to collect scattered light of said fabric upon said impingement.

The proposed system also comprises a wavelength division unit, a light detection unit; and a computing device (e.g. a server, a PC, a laptop, a Tablet, etc.) operatively connected with the light detection unit. The wavelength division unit is configured to separate the scattered light component into a plurality of spectral bands or colors, providing a plurality of signals of different wavelengths. The light detection unit is configured to detect the cited plurality of signals of different wavelengths and to convert them into electrical voltage signals.

Contrary to the known proposals, in the proposed system, the optical arrangement comprises a parabolic mirror with a hole and an optical device (e.g. an XY galvanometric mirror or a polygonal rotating mirror with equal or different angles between its faces and the rotating plane) located between the parabolic mirror and the fabric. The parabolic mirror is configured to allow the passage of the light beam towards the optical device via the hole, the collection and redirection of the scattered light component from the fabric towards said light detection unit, and the elimination of the light coming from direct reflection at the fabric through said hole.

Likewise, in the proposed system, the optical device is configured to change and dynamically orient the direction of the light beam towards the fabric providing a scan of an area of the fabric, line-by-line, and further configured to redirect the scattered light component from the fabric towards the parabolic mirror, the latter further redirecting the scattered light component towards the light detection unit. Besides, the computing device is configured to characterize a pattern marked on the fabric by executing an algorithm that analyzes the electrical voltage signals and that computes a quality measure of the marked pattern.

Preferably, the fabric is denim including black and color denim, for example a jeans, a shirt, shorts, a jacket, a vest, or a skirt. However, the system can be also used to characterize other fabrics such as Indigo knits, Knit, Brocade, Batiste, Canvas, Cashmere, Chambray, Chenille, Chiffon, Corduroy, Cotton duck/duck canvas, Crepe-back satin, Crepe de chine, Crochet, Damask, Fur, Faux fur, Felt, Flannel, Fleece, Gabardine, Gauze, Gazar, Georgette, Gingham, Grosgrain, Herringbone, Houndstooth check, Jersey, Jacquard, Lace, Lame, Leather, Linen, Madras, Microfiber, Mohair Mousseline, Neoprene, Nylon, Net, Organdie, Organza, Ottoman, Oxford, Paisley, Percale, Piqué, Plissé, Polar fleece, Poplin, Quilting, Rib knit, Ripstop, Sateen, Seersucker, Shantung, Sharkskin, Silk, Suede, Taffeta, Tartan, Toile, Tricot, Tweed, Twill, Velour/velvet, Vynil coated polyester, Viyella or Voile.

According to the present invention, the pattern can be marked by laser radiation, by an abrasion technique or product, by chemical means/elements, or may be due to an ageing or wear process or by any method of fabric finishing.

In an embodiment, the light detection unit comprises a series of optical detectors. According to the proposed system, each optical detector can be dedicated to detect one of said plurality of signals or a group of optical detectors can be dedicated to detect one of said plurality of signals. Hence, the optical detectors convert the optical signals of different wavelength into the cited electrical voltage signals. The computing device also includes an electronic device, such as an oscilloscope, configured to register the electrical voltage signals.

The optical detectors can be semiconductor photodiodes, avalanche photodiodes, thermopile sensors, pyroelectric sensors, photoconductors, balanced amplified detectors, photomultipliers, and quantum cascade detectors, among others. More particularly, the optical detectors can be semiconductor photodiodes or avalanche photodiodes of Silicon for visible and near-infrared range of 200-1100 nm, Indium Gallium Arsenide and/or Germanium for near and shortwave infrared range of 800-2600 nm, Mercury Cadmium Telluride for mid-infrared range of 2600-5500 nm, or Indium Antimonide for mid-infrared range 5400-7300 nm.

In an embodiment, the wavelength division unit and the light detection unit are configured to be combined forming a spectrometer.

The wavelength division unit can comprise any of a prism, a dichroic mirror, a grism, a transmissive diffraction grating, a reflective diffraction grating, a wavelength dependent interferometric filter including a low-pass, a high-pass, a band-pass or a notch, a linearly variable interferometric filter, or an absorption filter, or combinations thereof, among others.

The light source may include any of: a supercontinuum light source comprising a broadband emission wavelength range between 450 and 2400 nm; a visible enhanced supercontinuum source comprising at least the whole visible range from 400 nm to 750 nm; or a supercontinuum based in optical fibers made of soft-glass materials including chalcogenide glasses of elements Sulfur, Selenium, or Tellurium or fluoride glasses including ZBLAN fluoride glass, providing emission ranges from 2 μm to 15 μm.

In an embodiment, the plurality of spectral bands or colors comprises three different colors (red, green and blue, or RGB). Alternatively, the spectral bands comprise a single signal comprising the whole VIS-band or the whole NIR band or the whole SWIR band or the whole MID-IR band.

Preferably, the parabolic mirror is concave and has a focal length of approximately 101 millimeters with a 90° configuration.

Present invention also provides according to a second aspect a method for characterization of patterns marked on a fabric, the method comprising:

generating a light beam to impinge on a fabric (e.g. denim, among others) located at a given distance by a light source having a broadband spectrum (e.g. a supercontinuum light source);

directing the light beam towards the fabric by an optical arrangement comprising a parabolic mirror with a hole and an optical device located between the parabolic mirror and the fabric, the optical arrangement also collecting scattered light of the fabric upon said impingement;

changing and dynamically orienting, by the optical device, a direction of the light beam towards the fabric scanning an area of the fabric, line-by-line;

redirecting a scattered light component of the fabric towards the parabolic mirror, the latter further redirecting the scattered light component towards a wavelength division unit;

separating, by the wavelength division unit, the scattered light component into a plurality of spectral bands or colors, providing a plurality of signals of different wavelength;

detecting, by the light detection unit, the plurality of signals of different wavelength and converting them into electrical voltage signals; and characterizing, by a computing device operatively connected with the light detection unit, a pattern marked on the fabric by implementing an algorithm that analyzes the electrical voltage signals and that computes at least one quality measure of the marked pattern.

In the proposed method, the parabolic mirror allows the passage of the light beam towards the optical device via the hole, the collection and redirection of the scattered light component from the fabric towards a light detection unit, and the elimination of the light coming from direct reflection at the fabric through said hole.

Moreover, the scanning of the area of the fabric can be performed while the fabric and/or the optical device is/are moving.

According to an embodiment, the analysis includes a correction, performed by a self-referenced measurement, of the deviations of measured voltage values of the electrical voltage signal due to an angular position of the fabric. In particular, the self-referenced measurement is based in the calculation of a contrast between measured voltage values of marked points of the fabric and measured voltage values of unmarked points of the fabric (i.e. crude fabric).

According to an embodiment, the marked pattern comprises a striped pattern. In this case, the contrast between the measured voltage values of the striped pattern is determined by a visibility parameter, i.e. a mathematical fractional relation between the measured voltage values of the marked points of the fabric and the measured voltage values of the points of the crude fabric (i.e. not marked).

In a first example, the visibility parameter v is defined as $v=(V-B)/(V+B)$, where V and B are electrical voltage magnitudes referred to the marked and crude stripes respectively. In a second example, the visibility parameter is defined as the Weber's contrast p calculated as $p=(V-B)/B$.

According to an embodiment, the algorithm performs a Fourier frequency analysis of the measured voltage values to identify and remove possible aliasing components in the marked pattern.

Preferably, the pattern is marked by laser radiation. According to an embodiment, the algorithm calculates a visibility curve of the marked pattern, that is, a value of the visibility parameter of the marked pattern as function of a time of exposure of the marking laser on the fabric, or as function of an optical intensity of the marking laser on the fabric, or as function of a scanning velocity of the marking laser on the fabric.

The visibility curve can be calculated from a striped marked pattern including a given number of stripes, where each stripe is marked with a different exposure time by increasing the exposure time in regular steps from a minimum to a maximum time.

Different calculations can be obtained from the calculated visibility curve. For example, the algorithm can determine a number of visible stripes to human eye and a visibility threshold value below which the stripes are considered non visible for the human eye. Besides, the algorithm can determine an ideal visibility curve that laser marking parameters of exposure time and intensity should provide for a given fabric. Likewise, the algorithm can determine a White Quality of the marked pattern, which is obtained by comparison with measured voltages values obtained from a reference fabric selected as Pure White Fabric. Also, the algorithm can determine an equalization equation of the exposure time, or of the intensity or of the scanning velocity of the marking laser, so that the marked pattern matches a predefined shape. Even, the algorithm can optimize the time of marking laser exposure to match a predefined shape.

According to an embodiment, the algorithm provides a spatial two-dimensional map of voltages where each position on said map corresponds to a position of illumination in the fabric and the magnitude of the voltage in each position on the map corresponds to a scattered optical intensity detected from said corresponding point of illumination of the fabric, such that the spatial two-dimensional map of voltages provides an image of the marked pattern.

The spatial two-dimensional voltage map obtained from an arbitrary pattern marked on the fabric, preferably by natural wear or ageing, can also be used to reproduce said arbitrary pattern in another fabric, preferably by laser marking.

According to yet another embodiment, the algorithm provides a formula with arbitrary weighting factors to compute a quality parameter by analyzing three voltage levels respectively obtained from a sample of marked fabric of the fabric, from a sample of crude fabric of the fabric and from a white pure reference fabric.

Other embodiments of the invention that are disclosed herein also include according to another aspect software programs to perform the method embodiment steps and operations summarized above and disclosed in detail below. More particularly, a computer program product is one embodiment that has a computer-readable medium including computer program instructions encoded thereon that when executed on at least one processor in a computer system causes the processor to perform the operations indicated herein as embodiments of the invention.

BRIEF DESCRIPTION OF THE DRAWINGS

The previous and other advantages and features will be more fully understood from the following detailed description of embodiments, with reference to the attached figures, which must be considered in an illustrative and non-limiting manner, in which.

DETAILED DESCRIPTION OF EMBODIMENTS

Figure 1:
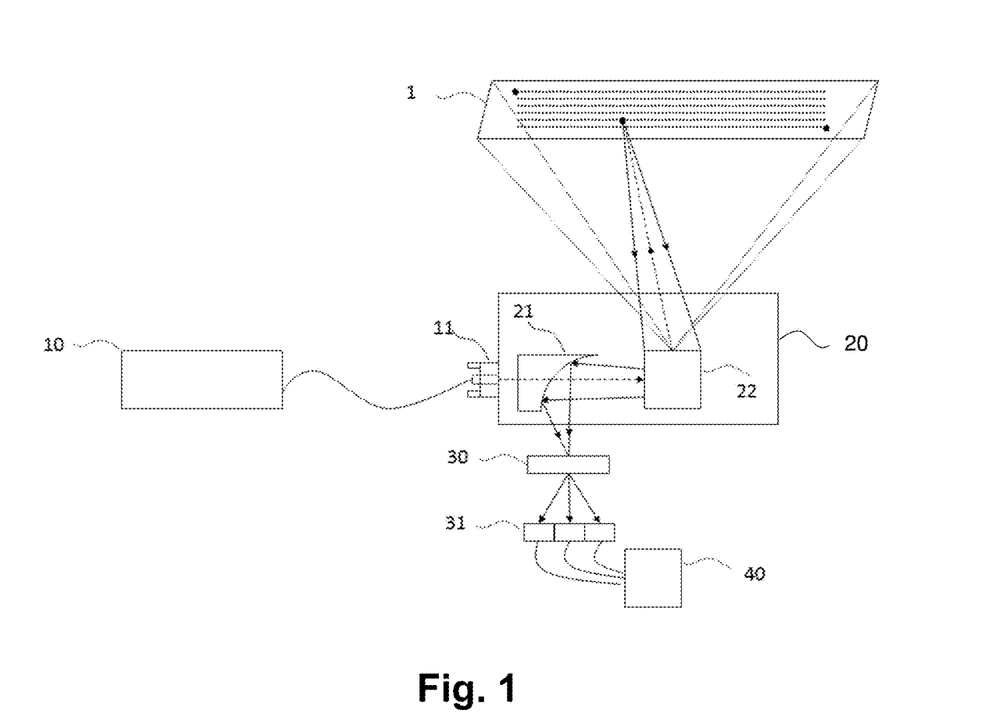
FIG. 1 is a schematic illustration of an embodiment of the proposed system for characterization of patterns marked (or generated) on a fabric.

FIG. 1 shows a preferred embodiment of the proposed system for characterization of patterns marked on a fabric. As shown in the figure, the proposed system includes a light source 10 configured to generate a light beam with a broadband spectrum to impinge on a fabric 1, preferably denim, located at a given distance; an optical arrangement 20 configured to direct the light beam towards the fabric 1 and to collect scattered light of the fabric 1 upon the impingement; a wavelength division unit 30; a light detection unit 31 and a computing device 40 with one or more processors and at least one memory, operatively connected to the light detection unit 31.

With the proposed system, the acquisition of a measurement and its subsequent analysis takes generally less than 10 seconds. This time can be as short as 2 or 3 seconds.

Although the fabric 1 is preferably denim other patterns generated/marked on other types of fabrics can be also characterized by the proposed system and method, for example Indigo knits, Knit, Brocade, Batiste, Canvas, Cashmere, Chambray, Chenille, Chiffon, Corduroy, Cotton duck/duck canvas, Crepe-back satin, Crepe de chine, Crochet, Damask, Fur, Faux fur, Felt, Flannel, Fleece, Gabardine, Gauze, Gazar, Georgette, Gingham, Grosgrain, Herringbone, Houndstooth check, Jersey, Jacquard, Lace, Lame, Leather, Linen, Madras, Microfiber, Mohair Mousseline, Neoprene, Nylon, Net, Organdie, Organza, Ottoman, Oxford, Paisley, Percale, Piqué, Plissé, Polar fleece, Poplin, Quilting, Rib knit, Ripstop, Sateen, Seersucker, Shantung, Sharkskin, Silk, Suede, Taffeta, Tartan, Toile, Tricot, Tweed, Twill, Velour/velvet, Vynil coated polyester, Viyella or Voile.

Moreover, the pattern is preferably marked by laser radiation, for example using a $CO_2$ laser. It should be noted that other type of lasers can also be used, for example other gas lasers (such as Argon-ion lasers), solid-state lasers (such as Nd:YAG or Ti:sapphire lasers), semiconductor diode lasers (such as GaAs or AlGaAs diode lasers); or fiber lasers (such as Yb, Er/Yb, Er or Tm fiber lasers). Alternatively, the pattern can be marked by an abrasion technique or product, by chemical means, may be due to an ageing or wear process, or can be marked by any method of fabric finishing.

The light source 10 may be any of a supercontinuum light source having a broadband emission wavelength range between 450 and 2400 nm, a visible enhanced supercontinuum source comprising at least the whole visible range from 400 nm to 750 nm, or a supercontinuum based in optical fibers made of soft-glass materials including chalcogenide glasses of elements Sulfur, Selenium, or Telurium or fluoride glasses including ZBLAN fluoride glass, providing emission ranges from 2 μm to 15 μm.

The wavelength division unit 30 can be a prism, a dichroic mirror; a grism; a transmissive diffraction grating; a reflective diffraction grating; a wavelength dependent interferometric filter including a low-pass, a high-pass, a band-pass or a notch; a linearly variable interferometric filter; or an absorption filter, or combinations thereof.

According to the preferred embodiment, the optical arrangement 20 comprises a parabolic mirror 21 with a hole and an optical device 22, such as an XY galvanometric mirror or a polygonal rotating mirror with equal or different angles between its faces and the rotating plane, located between the parabolic mirror and the fabric. The parabolic mirror is configured to allow the passage of the light beam towards the optical device 22 via the hole, the collection and redirection of the scattered light component from the fabric 1 towards said light detection unit 31, and the elimination of the light coming from direct reflection at the fabric 1 through said hole. Preferably, the parabolic mirror 21 is concave and has a focal length of approximately 101 millimeters with a 90° configuration.

The optical device 22 is configured to change and dynamically orient the direction of the light beam towards the fabric 1 providing a scan of an area of the fabric 1, line-by-line, and to redirect the scattered light component from the fabric 1 towards the parabolic mirror 21, the latter further redirecting the scattered light component towards the light detection unit 31. The scattered light component is separated by the wavelength division unit 30 into a number of spectral bands or colors, providing a series of signals of different wavelengths.

The computing device 40 is configured to characterize the pattern, or patterns, marked (or generated) on the fabric 1 by executing an algorithm that analyzes one or more of said signals and that computes one or more quality measures of the marked pattern, e.g. the brightness contrast between parts of the pattern, the number of observable stripes of a striped pattern, the visibility curve of a striped pattern, a comparison with a pure white, etc.

According to the preferred embodiment, the light detection unit 31 includes a series of optical detectors, such as semiconductor photodiodes, avalanche photodiodes, thermopile sensors, pyroelectric sensors, photoconductors, balanced amplified detectors, photomultipliers, and quantum cascade detectors, among others. More particularly, the optical detectors can be semiconductor photodiodes or avalanche photodiodes of Silicon for visible and near-infrared range of 200-1100 nm, Indium Gallium Arsenide and/or Germanium for near and shortwave infrared range of 800-2600 nm, Mercury Cadmium Telluride for mid-infrared range of 2600-5500 nm, or Indium Antimonide for mid-infrared range 5400-7300 nm, among others.

Each optical detector can be dedicated to detect one of said series of signals. Alternatively, a group of optical detectors of the series of optical detectors is dedicated to detect one of said series of signals. Moreover, the optical detectors are configured to convert the optical signal into an electrical voltage signal, i.e. the signal that is analyzed by the algorithm.

The computing device 40 preferably includes (not illustrated in the figure) an oscilloscope to register the electrical voltage signal as function of time. It should be noted that other types of electronic devices can be used to register the electrical voltage signal instead of an oscilloscope.

According to a preferred embodiment of the present invention, taking a measurement of the marked pattern on the fabric 1 means moving the light beam of a supercontinuum source 10 along the surface of the fabric 1 using the optical device 22 placed at a certain distance from the fabric 1. A user defines the scanning area, the number of lines per scanning and the sample points per line. Once the scanning is performed, the data is saved in the computing device 40, for example as a .csv file. These files contain a first row of data corresponding to the sampling time used in the oscilloscope. This row is stored as a Time Vector. The rest of the matrix (Sample Trace) corresponds to the measured electrical voltage signal from fabric 1. Depending on the final purpose of the measurement, the Sample Trace is averaged to a single vector (when an average of the sample is required) or kept as a matrix to analyze spatial-dependent information.

Figure 2:
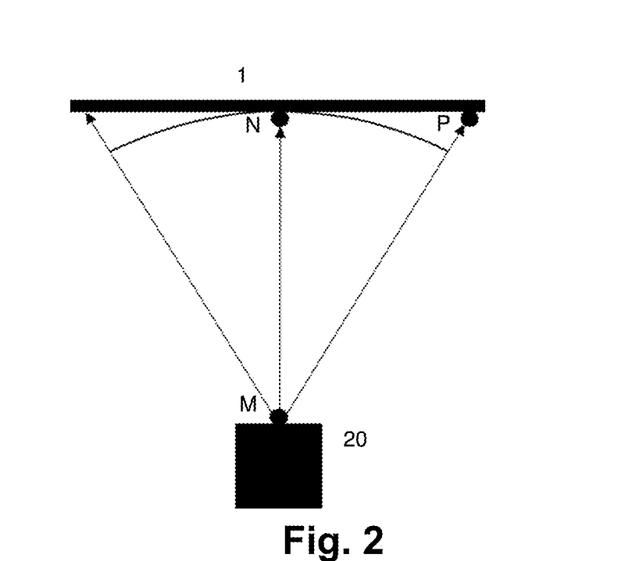
FIG. 2 illustrates the different distances from points of the fabric to the optical device, that imply the need of measurement correction for each angular position of the points.

Independently of the purpose of the measurement/characterization, there is one important aspect to consider for a correct data analysis of the signal. The distance between the fabric 1 and the optical device 22 is fixed, and thus, the backscattered light coming from different points of the fabric 1 will be at different distances to the optical device 22. As shown in FIG. 2, the distances between points $\overline{MN}$ and $\overline{MP}$ are different, leading to differences of intensity in the optical detector(s) 31 when the backscattered light signals from points M and P are the same. As the essence of the system consists of measuring signal variations among parts of the fabric 1 that have been marked differently, a calibration that implements an angle-dependent correction is performed. A general solution consists of making two different measurements. The calibration is made using the same fabric in crude, i.e. without being marked. By comparison, the signal collected from the marked fabric is angle-corrected. However, this solution may have some drawbacks. First, the two calibration steps increment the amount of time per measurement. Second, it may be affected by local differences between the calibration and marked fabrics such as wrinkles. And third, the access to a second crude fabric might not be available.

A different solution is implemented to make the measurement self-referenced. Preferably, a striped pattern is codified (marked) on the fabric 1, in this particular case by a $CO_2$ laser (not limitative since as has been indicated before the pattern may have been marked/generated by other techniques or with other types of lasers), alternating grey and crude stripes. The size of the stripes is small enough to make the following approximation: the brightness variation in a period distance shows a linear behavior. This concept is graphically explained in FIG. 3. The solid and dashed lines represent typical retrieved electrical voltage signals from the fabric 1. The retrieved signal by means of the proposed system decreases at the sides of the fabric 1 due to the geometrical configuration previously explained. The marked stripes produce a higher electrical voltage signal than the crude parts of the fabric 1 that have not been marked (considered also as a background). Therefore, the upper dashed line corresponds to the electrical voltage curve measured if the whole pattern would be marked homogeneously. On the other hand, the bottom dashed line simulates the electrical voltage measured when the whole fabric 1 is kept in crude. When the fabric 1 is marked using a stripe pattern, an electrical voltage trace such as the solid line is obtained. The need for calibration is then clearly shown: fabric parts with the same properties give different electrical voltage values. To measure the visibility of each stripe, the marked area is scanned by creating an oscillating line from left to right which is moved from top to the bottom of the fabric 1. The signal is then averaged to obtain a single data vector similar to the solid line of FIG. 3.

Figure 3:
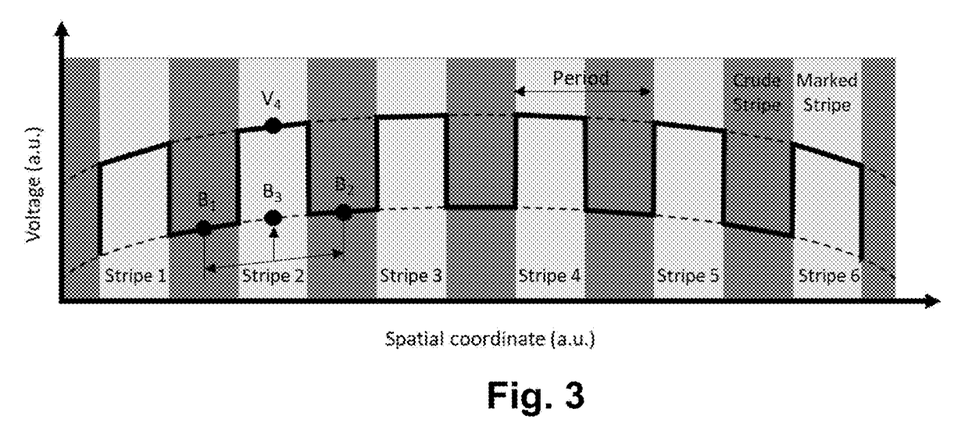
FIG. 3 illustrates the measured voltage obtained from a striped pattern marked on the fabric.
Figure 4:
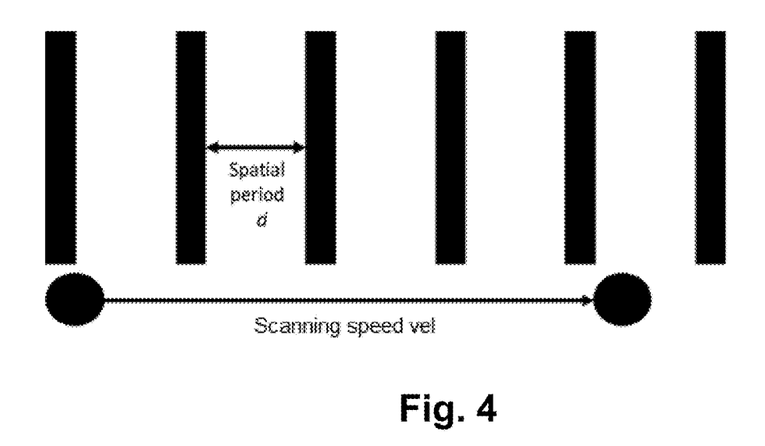
FIG. 4 illustrates the effect of the scanning speed over a periodic structure in the fabric.

The electrical voltage signal is treated to measure the visibility (contrast) of each stripe. The analysis, in an embodiment, is performed following the visibility v definition used in interferometric optical schemes. It is defined as:

$$v = \frac{V-B}{V+B} \quad [1]$$

where V and B are electrical voltage magnitudes referred to the marked and crude stripes respectively. Following the notation shown in FIG. 3, the visibility of the stripe number 2 is:

$$v_{\#2} = \frac{V_4 - B_3}{V_4 + B_3} \quad [2]$$

where $$B_3 = \frac{B_1 + B_2}{2} \quad [3]$$

As shown in the previous equation, the electrical voltage value $B_3$ is calculated supposing a linear electrical voltage variation between $B_1$ and $B_2$.

In the same way, different definitions of the contrast among the marked and crude parts of the fabric 1 can be made. This is the case of the so-called Weber's contrast, calculated as:

$$p = \frac{V-B}{B} \quad [4]$$

At this point, some computational effort must be done to detect the stripes in an automatic way, being independent of the fabric 1, performed laser marking or number of stripes. To distinguish crude and marked stripes, the algorithm detects change points, such as abrupt transitions in the mean or the variance, corresponding to the interface between a crude stripe and a marked stripe. To find a signal change point, the mathematical function employs a parametric global method. The function follows the next steps:

Chooses a point and divides the signal into two sections.
Computes an empirical estimate of the desired statistical property for each section.
At each point within a section, measures how much the property deviates from the empirical estimate, and then adds the deviations for all points.
Adds the deviations section-to-section to find the total residual error.
Varies the location of the division point until the total residual error attains a minimum.

The algorithm can be customized to discard abrupt transitions attributable to local variation in the fabric 1, so that it only detects change points in those positions where the stripes have been codified.

Once the change points are detected, the algorithm calculates the signal corresponding to each stripe. This value corresponds to an average of all the signals integrated during the scanning for each stripe area. The calculation results in a 3*N set of data (corresponding to the crude and marked stripes, and its position on the fabric 1), being N the number of codified stripes.

On the other hand, the user may not need to measure the visibility of different marked stripes, but is interested in retrieving spatial information from the fabric 1. In this case, the Sample Trace is not averaged, and the resultant two-dimensional matrix is plotted resulting in a point to point laser-based image of the fabric 1. This concept is explained later ('2D MAP of the fabric').

At this point, and for both the averaged and raw data, a Fourier frequency analysis can be performed to study the frequency patterns presented in the fabric 1, as well as to identify possible aliasing patterns coming from the pulsed nature of the supercontinuum light source 10 in combination with the cutoff frequency of the photodetector(s) and the sampling time in the oscilloscope.

When the marked pattern contains a periodic structure, the Fourier frequency analysis shows this behavior at a specific frequency depending on the scanning speed vel over the fabric 1 and the nature of the periodic structure (its spatial period d, see FIG. 3).

Therefore, the details of the fabric 1 will appear at a frequency $f_d$ calculated as:

$$f_d = \frac{1}{t} = \frac{vel}{d} \quad [5]$$

where t is the elapsed time for the laser spot to travel a distance d.

When the Fourier analysis is performed, a frequency component appears at the specific pulse repetition frequency of the supercontinuum source $f_{SC}$. The pulsed nature of the supercontinuum source 10 may complicate the further mathematical analysis of the signal, and it is convenient to eliminate it. Note that for Continuous Wave (CW) light sources this is not needed. If the frequency sampling $f_s$ established in the oscilloscope is smaller than $f_{SC}$, the frequency peak will not appear at the frequency $f_{SC}$, but at a different frequency ($f_{alias}$) defined by the Nyquist theorem due to an effect known as aliasing. Considering a sinusoid frequency approximation, and replacing negative frequencies by their equivalent positive frequency representations, all the aliases of frequencies can be expressed as $f_{alias}(N)=|f_{SC}-Nf_s|$ for any integer N. The effect of the aliasing frequency is similar to that of the supercontinuum pulse repetition frequency, showing frequencies that are not inherent to the analyzed fabric 1 and making the subsequent data analysis difficult.

For these cases a digital lowpass filter is implemented. The cutoff frequency $f_{cutoff}$ of the filter needs to be above the highest spatial frequency presented on the fabric 1 and below the pulse repetition frequency of the supercontinuum source 10 or the minimum aliasing frequency. Therefore, $f_d < f_{cutoff} < f_{SC/alias}$. This a post-processing solution based on a digital filtering of the signal (software). An alternative solution consists of designing a voltage sensor that implements an analogic filter to the signal (hardware). Both solutions have been successfully implemented, filtering the measured signal and keeping just that information which is useful.

Data Analysis.—

In an embodiment, for the calculations, a stripe grey pattern from 0 to 255 (integer values) is codified in the fabric 1 by means of the $CO_2$ laser. Each grey level refers to a different marking time, being 0 the highest marking time and 255 the lowest. The stripe pattern starts in the zero level and ends in the 250 level, with a step of 10 grey levels, resulting in 26 stripes.

Figure 5:
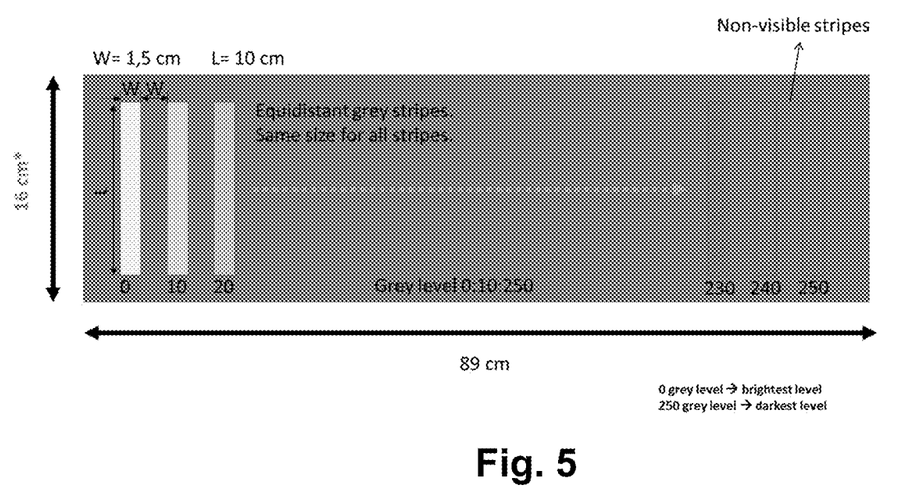
FIG. 5 illustrates a striped pattern marked in two dimensions on the fabric.

In FIG. 5, a typical stripe pattern is shown. The brightest stripe is placed to the left, and the brightness level of the stripes goes down as the last stripe (corresponding to the grey level 250) is approximated. In general, the brightness variation with grey level is not linear and may decay before 250 to a level that is not visible to human eye.

Visibility Curve.—

Figure 6:
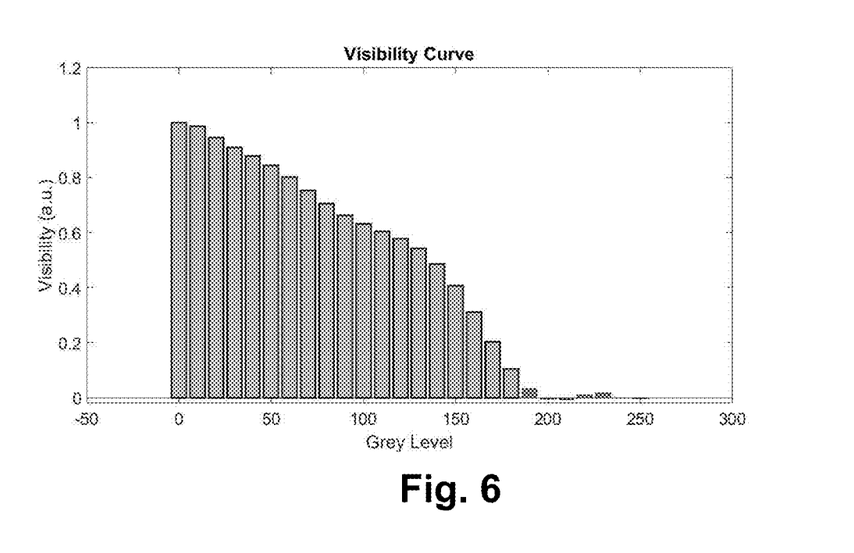
FIG. 6 illustrates an example of the calculated visibility curve obtained from a fabric marked with a striped pattern.
Figure 7:
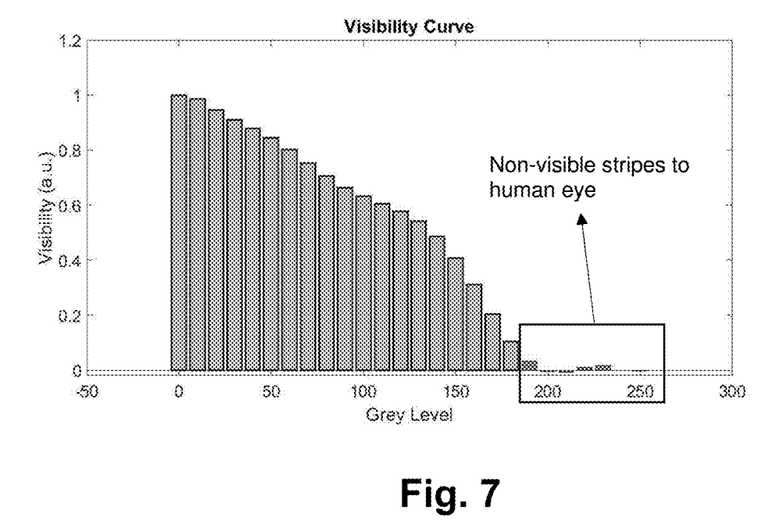
FIG. 7 shows the non-visible stripes to human eye calculated from the visibility curve of FIG. 6.
Figure 8:
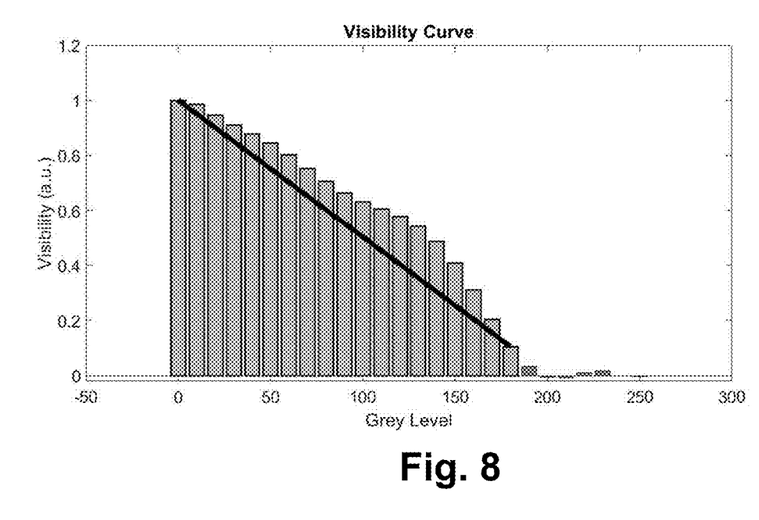
FIG. 8 illustrates the visibility curve of FIG. 6 compared to an ideal visibility curve (solid line) for which the dependence of visibility as function of grey level (GL) is linear.

In an embodiment, a visibility value is calculated for each marked stripe according to Eq. [1], with a total of 26 values. A plot of the visibility versus the grey level is given to the user. The 26 points are fitted to a high-grade polynomial in order to adjust the fabric response to laser marking for all the grey levels, resulting in a final vector of 256 values. The visibility curve is plotted in FIG. 6, where it is shown normalized to 1.

Weber's Visibility Curve.—

In an embodiment, a Weber's visibility value is calculated for each marked stripe according to Eq. [4], with a total of 26 values. A plot of the visibility versus the grey level is given to the user. As in the previous case, the 26 points are fitted to a high-grade polynomial in order to adjust the fabric response to laser marking for all the grey levels, resulting in a final vector of 256 values.

Number of Visible Stripes.—

Based on the results obtained for the visibility curve defined in Eq. [1], the number of visible stripes to human eye can be calculated. From the study of large amounts of marked fabrics, one or more visibility threshold values ($V_{th}$) are estimated. The stripes with visibility values below $V_{th}$ are discriminated as non-visible.

Ideal Slope.—

The visibility curves derived from Eq. [1] or Eq. [4] are different for each fabric 1. The ideal dependence between the visibility curves and the grey level would be a linear one, ranging from 0 to 255. However, in many occasions, the last visible grey level corresponds to a value quite below 255. Therefore, two comparisons are made. The first one compares the obtained curve with a linear distribution from 0 to 255. The second one compares the obtained curve with a linear distribution from 0 to the grey level corresponding to $V_{th}$. The criteria to characterize the visibility curve shape englobe different approximations such as: the sum of squares due to error (SSE), the R-square, the Adjusted R-square, the Root mean squared error (RMSE), the derivative of the chosen function used to relate the visibility and the GL, the Chi-squared test, the Kolmogorov-Smirnov test, the Cramer-von Mises criterion, the Anderson-Darling test, the Shapiro-Wilk test, the Akaike information criterion, the Hosmer-Lemeshow test, the Kuiper's test or the kernelized Stein discrepancy.

Although a linear behavior is quite often demanded, the user can evaluate the similarity of the visibility curve to any other distribution by simply redefining the ideal behavior.

White Quality.—

The visibility curves give information about the contrast of the marked pattern with the crude fabric. However, stripes with the same brightness level (V in Eq. [1]) may result in quite different visibility values because they are marked on different fabrics (which have different B values). To have an absolute estimation of the brightness level of each stripe, they are compared to an ideal white fabric used for calibration. The measure is called white quality (WQ), and can be calculated as:

$$WQ = \frac{V}{V_W}, \quad [6]$$

where $V_W$ represents the voltage value of the white fabric used for calibration. As shown in FIG. 3, it is crucial to match the angular position of each stripe to the same angular position of the white calibration fabric. Therefore, the value $V_W$ is not constant; it is angular dependent and can be calculated for each stripe.

Measure Falling Curve for Crude Fabric.—

The proposed system can be also used to study the scattering properties of the crude fabrics. The data taken from the scanning is averaged to one vector and the curves are compared. Differences in the curvature of the signal provide information about the optical properties of the fabric 1, which can be ultimately related to each composition.

Fabric Sorting.—

The results previously obtained in an embodiment are weighted to determine the response of each fabric to laser marking. Not all the fabrics have the same response to laser marking, and it is important to sort them as a function of its suitability to get designs that can be marked. There are several parameters that are important to take into account.

The first one is the visibility as defined in Eq. [1]. The industry pursues patterns with high contrasts, so the higher the v the better the fabric will be considered.

The second one is the WQ defined in Eq. [6]. Independently of the contrast, the maximum absolute electrical voltage measured for a specific fabric, and its comparison with a pure white fabric, is reliable in the industry. Those fabrics that allow reaching high values of WQ are better considered for laser marking designs in comparison with those that give low WQ values.

The third one is related with the shape of the visibility curve. In general, a constant slope of the curve is preferred by the user, so that the final design presents a linear dependence with GL, which is the parameter used by the designers to create the pattern. Other dependences between the visibility and the GL might be also desired. How the visibility curve falls, in comparison with the criterion previously defined by the user, is an additional parameter to consider when estimating the quality of a specific fabric for laser marking purposes.

The visibility v, the WQ and the study of the visibility curve are, in many cases, enough to determine the quality of the fabric 1. However, the visibility v and the WQ tend to misinterpret those crude fabrics that are either very dark or very bright. These properties of the crude fabrics are related to the B electrical voltage from Eqs. [1] and [4], being low for dark fabrics and high for bright ones. The misinterpretation is mainly due to the visibility v, which is extremely high for dark fabrics and extremely low for bright fabrics. Dark and bright fabrics behave in a different way and the industry assumes this fact. Therefore, it is important to consider as well another parameter to determine the quality of the fabric 1 in order to avoid the penalization of bright fabrics and the overestimation of dark ones. This value is explained in FIG. 9, where a 3-level study is proposed.

Figure 9:
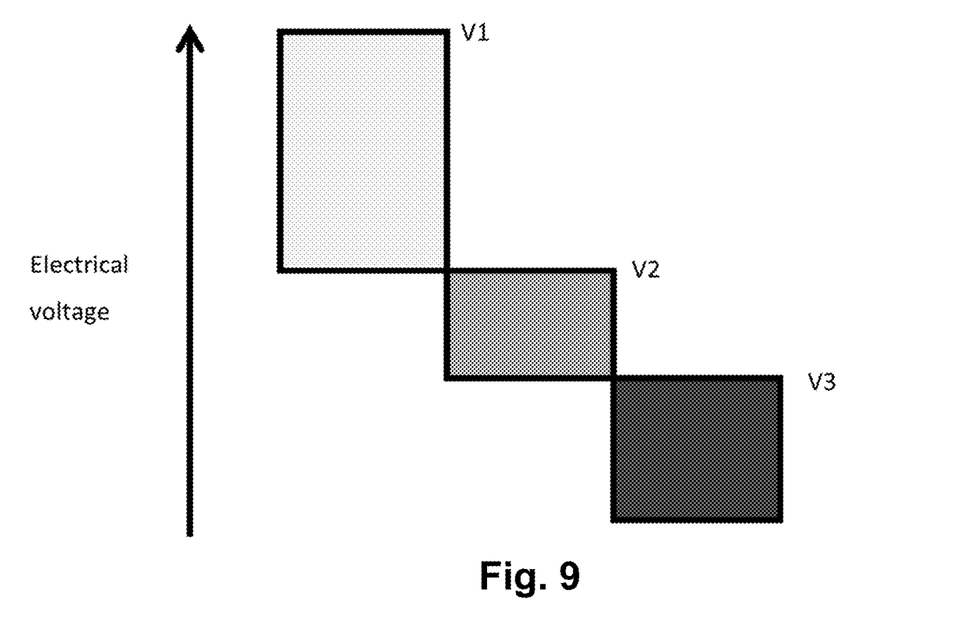
FIG. 9 shows a representation diagram of the 3-level study to calculate the quality of the fabric.
Figure 10:
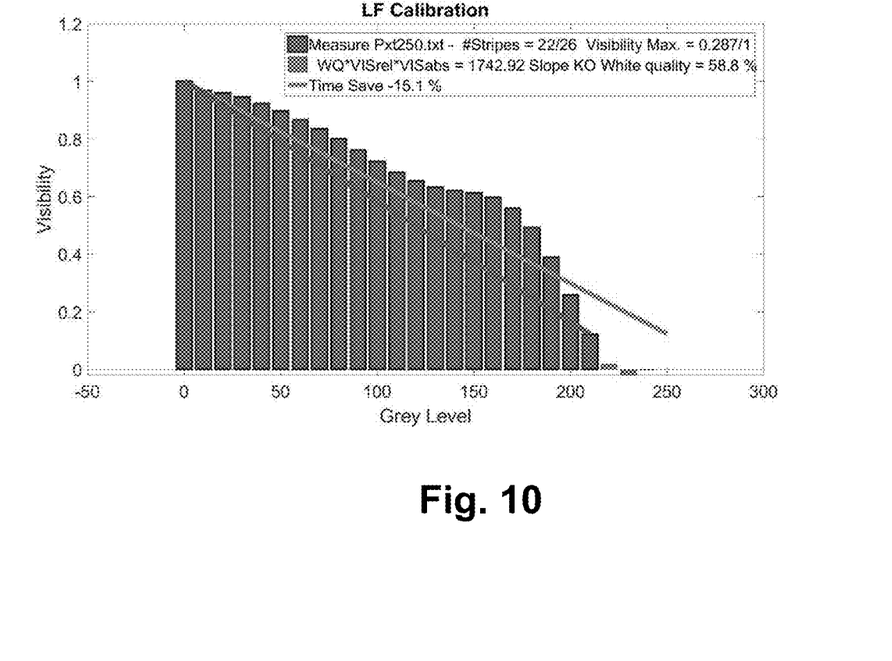
FIG. 10 is the visibility curve of a fabric marked using the definition of Period of Eq. [7].
Figure 11:
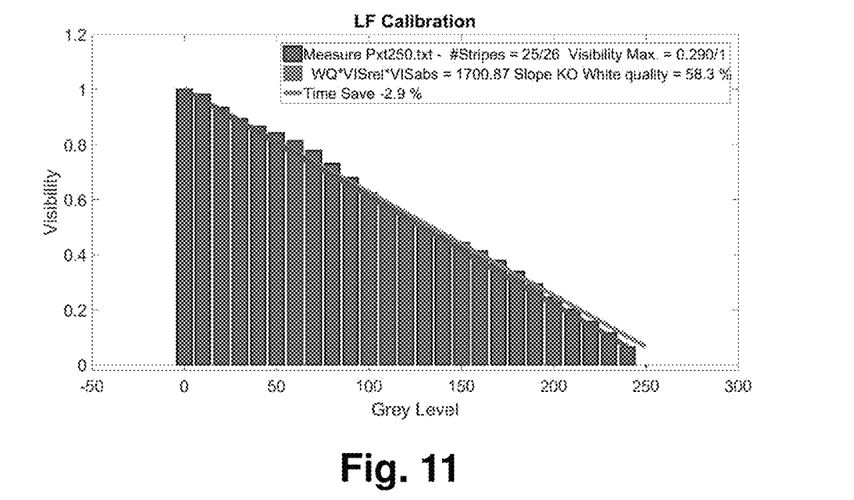
FIG. 11 is the visibility curve of the same fabric of FIG. 10 after equalizing the parameter pxt to obtain a linear shape for the visibility curve.
Figure 12:
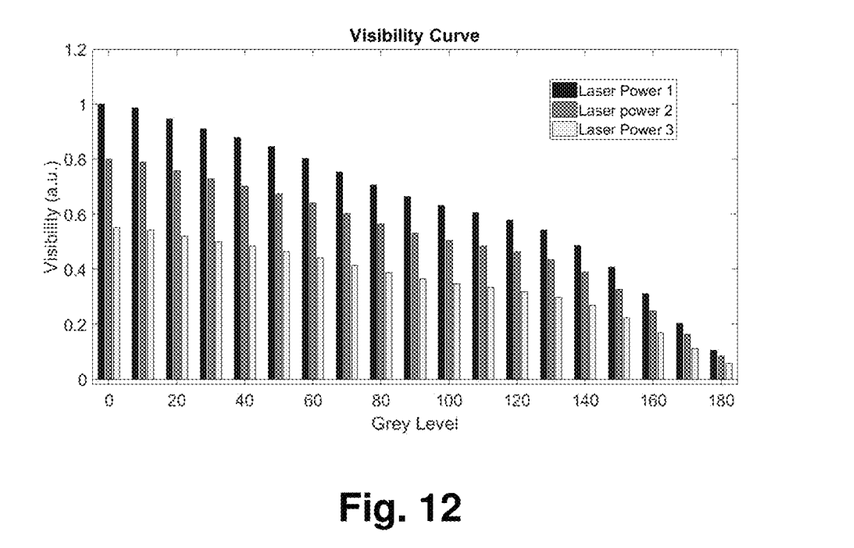
FIG. 12 graphically illustrates an example of the visibility curves obtained by marking a fabric with a $CO_2$ laser operating with different average output powers under same conditions of exposure time.

The values V1, V2, and V3 correspond, respectively, to the electrical voltage signal retrieved from the pure white fabric used for calibration, from a sample of the marked pattern on the fabric 1 and from a sample of the crude fabric (background).

In this way, the visibility v would be equal to (V2−V3)/(V2+V3) and the WQ equal to V2/V3. However, as previously mentioned, these values do not directly take into account whether the V3 is low or high, that is to say, how dark or bright the fabric 1 is before being marked. To do so, two additional parameters are considered:

The V3 electrical voltage.

The percentage of signal that is increased with respect to the available dynamic range: (V2−V3)/(V1−V3). This parameter is called the dynamic range contrast (DRC).

With all these parameters, a general theoretical punctuation can be calculated for each fabric by the function defined below:

$$\text{Punct}=f(v,WQ,DRC,V3)$$

where the parameters v, WQ, DRC and V3 in the function Punct are arbitrarily weighted according to the requirements of the designer.

Equalizing.—

In an embodiment, the marked pattern is configured by a 0 to 255 grey level (GL) image. The 0 level corresponds to the brightest GL marked on the fabric 1, while 255 corresponds to the darkest. This grey scale is converted to a pixel time (pxt) value. The pxt makes reference to the time that the light source 10 spends in each pixel area in which the fabric 1 is divided, and it is usually measured in microseconds (µs). Therefore, the grey scale from 0 to 255 is converted to a temporal magnitude. Both scales are related by the following formula:

$$\text{Period} = pxt_{ini} * \left(1 - \frac{GL}{255}\right), \quad [7]$$

where Period is an array of 256 values corresponding to the marking time for each grey level GL. The value $pxt_{ini}$ is defined by the user, and refers to the initial pixel time corresponding to GL=0.

Eq. [7] establishes a linear dependence between the Period and the GL scale. However, in many occasions, the visibility curve defined as in Eq. [1] and shown in FIG. 6, does not behave in a linear way when it is marked following Eq. [7]. If a linear response for the visibility curve is pursued by the user (or, in general, any other response previously defined by the user as commented before), it is necessary to modify the Period multiplying it by an equalizing curve EQU:

$$\text{Pulse}=EQU*\text{Period}, \quad [8]$$

The new marking time for each grey level is called Pulse. When EQU is an array of ones, Pulse=Period.

In an embodiment, equalizing the $CO_2$ laser comprises calculating the right Pulse definition so that the marked pattern matches a shape predefined by the user. To do that, a first laser pattern is codified using a known GL to pxt algorithm (as Period from Eq. [7]). Therefore, a pxt to visibility relationship is obtained (v(pxt)). Then, the appropriate EQU is calculated so that the new marked pattern coincides with that previously defined by the user.

Power Calibration.—

The parameters that are involved in the generation of the pattern on the fabric 1 are those contained in Eq. [7] and [8]. Both equations only relate the amount of time (pxt) that the marking laser stays on each pixel area of the fabric 1. However, the pxt is ultimately linked to the laser energy that is deposited in each pixel area. If lasers with different average output powers are used, the generated patterns on the same fabric 1 will be different when the same definitions of Period or Pulse are used. Small differences in the average output power for two or more lasers of the same type will lead to noticeable variations in the visibility curved obtained for each one when marking under the same conditions. In this way, the visibility curve can be used as a sensitive method to monitor and calibrate lasers to generate repeatable patterns for all the lasers of the same type.

Time Consuming Optimization.—

The visibility curve is plotted against the GL, which can be related to marking time by Eq. [7] and [8]. In this way, an estimation of the marking time can be computed by adding all the pxt for each GL. The marking time is then:

$$t_{mark} = \sum_{GL=0}^{GL=255} \text{Period}(GL) \quad [9]$$

This time calculation supposes that all the GLs are presented in the design used to mark the fabric 1. A more accurate calculation can be done by modifying the weights of each summation's term in Eq. [9].

If the user equalizes the marking laser resulting a different marking time Pulse, then the new marking time $t'_{mark}$ can be calculated as in Eq. [9]:

$$t'_{mark} = \sum_{GL=0}^{GL=255} \text{Pulse}(GL) \quad [10]$$

Therefore, the difference between both marking times is calculated as:

$$\Delta t = t'_{mark} - t_{mark} \quad [11]$$

where the sign of $\Delta t$ defines whether a time saving is produced (negative) or not (positive).

2D MAP of the Fabric.—

As previously said, the raw data that results from a measure consists of a Time Vector and a Sample Trace. The Time Vector makes reference to the sampling time used in the oscilloscope to retrieve the electrical voltage signal from the fabric 1. The sampling time $t_s$ of the oscilloscope can be modified, reducing or increasing the number of points per line that are finally saved. In any case, it is important to consider that the sampling time is just the inverse of the mentioned frequency sampling $f_s$, and thus it must be taken into account to eliminate frequency issues as those exposed in section 1. The sampling time in the oscilloscope is translated to different spatial positions on the fabric 1. The conversion from time to spatial coordinates is easily calculated as:

$$\Delta d = d_1 - d_2 = vel^*(t_1 - t_2) = vel^* t_s \quad [12]$$

Figure 13:
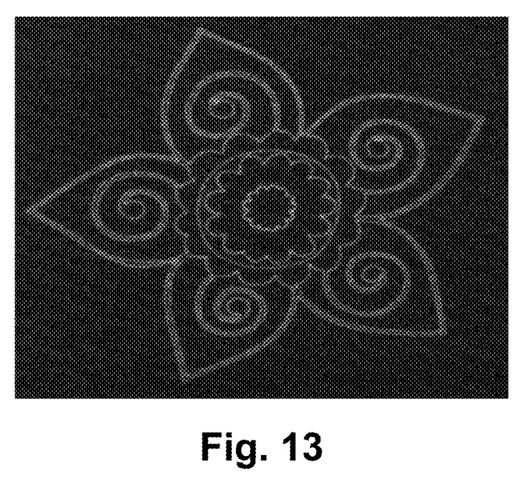
FIG. 13 shows an example of the 2D voltage map obtained from an arbitrary pattern marked (or generated) on a fabric.

This equation establishes a minimum in spatial resolution for the system. However, for a real estimation of the spatial resolution, the spot size of the beam of the light source 10 on the fabric 1 must be also considered. Equation [12] allows the conversion from temporal to spatial domain, and thus a "picture" of the fabric 1 can be displayed as shown in FIG. 13. It is important to note that the image is taken point by point at different times, where the only area that is illuminated at each time moment is that where the spot of the beam of the light source impinges.

Guess Design.—

The 2D map of the marked pattern can be used to extract marking information of unknown designs. The design of new jeans is frequently based on old jeans that have suffered wear. In this way, the designers try to digitalize the wear of those jeans for being able to reproduce the same forms by laser marking. This is usually a process that requires a high time consumption and relies on the skills of the designer to succeed.

The 2D map of the marked pattern is then used to extract the design of the jeans, digitalizing in an automatic way the pattern to be marked.

Frequencies Presented in the Sample.—

Many fabrics present a periodic texture. A frequency analysis of the measured pattern can be performed in order to determine which periodic structures are present on the sample. The sampling time $t_s$ used for measuring is known. Therefore, the spectral components are extracted by computing a discrete Fourier transform (DFT) of the Sample Trace using a fast Fourier transform (FFT) algorithm. The spectral analysis can be performed either to the averaged data or to the raw data. By means of Eq. [5] the real spatial period of the periodic structures presented on the sample (d) can be calculated as far as $f_a$ and vel are known.

While the foregoing is directed to embodiments of the present invention, other and further embodiments of the invention may be devised without departing from the basic scope thereof. For example, other aspects may be implemented in hardware or software or in a combination of hardware and software.

Additionally, the software programs included as part of the invention may be embodied in a computer program product that includes a computer useable medium. For example, such a computer usable medium can include a readable memory device, such as a hard drive device, a flash memory device, a CD-ROM, a DVD/ROM, or a computer diskette, having computer readable program code segments stored thereon. The computer readable medium can also include a communications link, either optical, wired, or wireless, having program code segments carried thereon as digital or analog signals.

The scope of the present invention is defined in the following set of claims.

The invention claimed is:

1. A system for characterization of patterns marked on a fabric, the system comprising:
   a light source configured to generate a light beam to impinge on a fabric located at a given distance, said light beam having a broadband spectrum;
   an optical arrangement configured to direct said light beam towards the fabricand to collect scattered light of said fabric upon said impingement;
   a wavelength division unit configured to separate a scattered light component into a plurality of spectral bands or colors, providing a plurality of signals of different wavelengths;
a light detection unit configured to detect said plurality of signals of different wavelengths and convert them into electrical voltage signals; and
   a computing device operatively connected with said light detection unit;
wherein:
   said optical arrangement comprises a parabolic mirror with a hole and an optical device located between the parabolic mirror and the fabric, said parabolic mirror allowing the passage of the light beam towards the optical device via the hole, the collection and redirection of the scattered light component from the fabric towards said light detection unit, and the elimination of the light coming from direct reflection at the fabric through said hole;
   the optical device is configured to change and dynamically orient the direction of the light beam towards the fabric providing a scan of an area of the fabric, line-by-line, and further configured to redirect the scattered light component from the fabric towards the parabolic mirror, the latter further redirecting the scattered light component towards the light detection unit; and
   the computing device is configured to characterize a pattern marked on the fabric by executing an algorithm that analyzes said electrical voltage signals and that computes a quality measure of said marked pattern.

2. The system of claim 1, wherein:
   the light detection unit comprises a series of optical detectors, wherein each optical detector of said series of optical detectors is dedicated to detect one of said plurality of signals and to convert the detected optical signal into an electrical voltage signal or wherein a group of optical detectors of the series of optical detectors is dedicated to detect one of said plurality of signals and to convert the detected optical signal into an electrical voltage signal; and
   the computing device includes an electronic device configured to register said electrical voltage signals.

3. The system of claim 1, wherein the wavelength division unit and the light detection unit are configured to be combined forming a spectrometer.

4. The system of claim 1, wherein the wavelength division unit comprises a prism, a dichroic mirror, a grism, a transmissive diffraction grating, a reflective diffraction grating, a wavelength dependent interferometric filter including a low-pass, a high-pass, a band-pass or a notch, a linearly variable interferometric filter, or an absorption filter, or combinations thereof.

5. The system of claim 1, wherein the light source comprises one of:
   a supercontinuum light source comprising a broadband emission wavelength range between 450 and 2400 nm;
   a visible enhanced supercontinuum source comprising at least the whole visible range from 400 nm to 750 nm; or
   a supercontinuum based in optical fibers made of soft-glass materials including chalcogenide glasses of elements Sulfur, Selenium, or Tellurium or fluoride glasses including ZBLAN fluoride glass, providing emission ranges from 2 µm to 15 µm.

6. A method for characterization of patterns marked on a fabric, the method comprising:
generating, by a light source, a light beam to impinge on a fabric located at a given distance, said light beam having a broadband spectrum;
directing, by an optical arrangement, said light beam towards the fabric and collecting scattered light of said fabric upon said impingement, said optical arrangement comprising a parabolic mirror with a hole and an optical device located between the parabolic mirror and the fabric, said parabolic mirror allowing:
the passage of the light beam towards the optical device via the hole,
the collection and redirection of a scattered light component from the fabric towards a light detection unit, and
   the elimination of the light coming from direct reflection at the fabric through said hole;

changing and dynamically orienting, by the optical device, a direction of the light beam towards the fabric, scanning an area of the fabric, line-by-line;

redirecting the scattered light component of the fabric towards the parabolic mirror, the latter further redirecting the scattered light component towards a wavelength division unit (30);

separating, by the wavelength division unit, the scattered light component into a plurality of spectral bands or colors, providing a plurality of signals of different wavelength;

detecting, by the light detection unit, said plurality of signals of different wavelength and converting them into electrical voltage signals; and characterizing, by a computing device operatively connected with the light detection unit, a pattern marked on the fabric by implementing an algorithm that analyzes said electrical voltage signals and that computes a quality measure of the marked pattern.

7. The method of claim 6, wherein said analysis includes a correction of the deviations of measured voltage values of said electrical voltage signal due to an angular position of the fabric, said correction being performed by a self-referenced measurement, and said self-referenced measurement is based in the calculation of a contrast between measured voltage values of marked points of the fabric and measured voltage values of unmarked points of the fabric.

8. The method of claim 7, wherein said marked pattern comprises a striped pattern, and wherein said contrast between the measured voltage values of the striped pattern is determined by a visibility parameter, said visibility parameter being determined by a mathematical fractional relation between said measured voltage values of the marked points of the fabric and said measured voltage values of the unmarked points of the fabric.

9. The method of claim 8, wherein said marked pattern is generated by laser radiation, and wherein the algorithm calculates a visibility curve of the marked pattern, said visibility curve being the value of said visibility parameter of the marked pattern as function of a time of exposure of the marking laser on the fabric, or as function of an optical intensity of the marking laser on the fabric, or as function of a scanning velocity of the marking laser on the fabric.

10. The method of claim 9, wherein:

said visibility curve is calculated from the marked pattern comprising a striped pattern, the latter including a given number of stripes, each stripe being marked with a different exposure time by increasing the exposure time in regular steps from a minimum to a maximum time; and/or from the calculated visibility curve, the algorithm determines a number of visible stripes to human eye and a visibility threshold value below which the stripes are considered non-visible for the human eye; and/or from the calculated visibility curve, the algorithm determines an ideal visibility curve that laser marking parameters of exposure time and intensity should provide for a given fabric; and/or from the calculated visibility curve, the algorithm determines a White Quality of the marked pattern, which is obtained by comparison with measured voltage values obtained from a reference fabric selected as Pure White Fabric; and/or from the calculated visibility curve, the algorithm determines an equalization equation of an exposure time, or of an intensity or of a scanning velocity of the marking laser, so that the marked pattern matches a predefined shape; and/or from the calculated visibility curve, the algorithm optimizes the time of exposure of the marking laser to match a predefined shape.

11. The method of claim 6, wherein the algorithm provides a spatial two-dimensional map of voltages, wherein each position on said map corresponds to a position of illumination in the fabric and the magnitude of the voltage in each position on the map corresponds to a scattered optical intensity detected from said corresponding point of illumination of the fabric, so that said spatial two-dimensional map of voltages provides an image of the marked pattern.

12. The method of claim 11, wherein the spatial two-dimensional voltage map obtained from an arbitrary pattern marked on the fabric is used to reproduce said arbitrary pattern in another fabric by laser marking.

13. The method of claim 6, wherein the algorithm comprises providing a formula with arbitrary weighting factors to compute a quality parameter by analyzing three voltage levels respectively obtained: from a sample of marked fabric of the fabric, from a sample of unmarked fabric of the fabric, and from a white pure reference fabric.

14. The method of claim 6, wherein said scanning of an area of the fabric is performed while the fabric and/or the optical device is/are moving.

15. The method of claim 6, wherein the fabric at least comprises denim.

* * * * *